United States Patent [19]
Miller et al.

[11] Patent Number: 5,221,269
[45] Date of Patent: Jun. 22, 1993

[54] GUIDE FOR LOCALIZING A NONPALPABLE BREAST LESION

[75] Inventors: Richard H. Miller, Pittsburgh, Pa.; Brian L. Bates, Bloomington, Ind.; Todd A. Hall, Bloomington, Ind.; Thomas A. Osborne, Bloomington, Ind.

[73] Assignee: Cook Incorporated, Bloomington, Ind.

[21] Appl. No.: 597,575

[22] Filed: Oct. 15, 1990

[51] Int. Cl.⁵ .............................................. A61M 25/00
[52] U.S. Cl. ................................... 604/281; 604/164; 604/264; 606/116
[58] Field of Search ...................... 606/108, 116, 180; 604/164-166, 264, 272-274, 281; 128/751, 753-754, 784-785, 657-658, 749

[56] References Cited

U.S. PATENT DOCUMENTS

| | | | |
|---|---|---|---|
| 2,022,065 | 11/1935 | Wappler . | |
| 2,047,535 | 7/1936 | Wappler . | |
| 3,330,278 | 7/1967 | Santomieri | 606/108 |
| 3,516,412 | 6/1970 | Ackerman | 128/418 |
| 3,890,977 | 6/1975 | Wilson | 128/418 |
| 4,103,690 | 8/1978 | Harris | 128/418 |
| 4,274,408 | 6/1981 | Nimrod | 606/108 X |
| 4,616,656 | 10/1986 | Nicholson et al. | 128/630 |
| 4,799,495 | 1/1989 | Hawkins et al. | 128/754 |
| 4,869,259 | 9/1989 | Elkins | 128/660 |
| 4,925,445 | 5/1990 | Sakamoto et al. | 604/95 |
| 5,018,530 | 5/1991 | Rank et al. | 128/749 |
| 5,122,136 | 6/1992 | Guglielmi et al. | 606/32 |

OTHER PUBLICATIONS

Urrutia, E. J. et al., "Retractable-Barb Needle for Breast Lesion Localization: Use in 60 Cases," *Radiology*, 169:845-847, 1988.

"Uncompromising Position: The Hawkins TM Breast Localization Needle Stays Put—Until you Decide Otherwise," N-S Medical Products, Gainesville, Fla.

"Namic Proudly Introduces the Homer Mammalok TM Needle/Wire Localizer", Namic, Sep. 1985.

"Disposable Kopans Breast Lesion Localization Needles" Cook Incorporated Product Catalog, 1986.

"The Hawkins TM Family of Breast Lesion Localization Needle/Wire Localizer", Medi-tech Boston Scientific Corporation, Watertown, Mass.

*Primary Examiner*—C. Fred Rosenbaum
*Assistant Examiner*—Corrine Maglione
*Attorney, Agent, or Firm*—Richard J. Godlewski

[57] ABSTRACT

A medical device for localizing a nonpalpable breast lesion. The device includes a tubular introducer needle and a wire guide positioned therein for inserting into a breast to the site of the lesion. The wire guide includes a distal portion having a preformed, resilient helical coil configuration for locking into position about the lesion. The distal portion includes a superelastic metallic alloy for maintaining the helical coil configuration after repeated extensions from and retractions into the needle passageway. The needle is inserted with the wire guide positioned therein into the breast to the site of the lesion and from the distal portion of the needle. The distal end of the needle includes a plurality of indentations for enhancing the ultrasound visualization thereof. As the distal portion of the wire guide emerges from the needle, the acuate distal end of the wire guide cuts into and scribes a helical path about the tissue distal to the lesion. The remainder of the distal portion of the wire guide follows the path scribed by the acuate distal tip and locks about the tissue distal to the lesion. Should the needle and wire guide not be appropriately positioned, the distal portion of the wire guide is retracted into the passageway of the needle to reposition the needle and guide. After desired positioning, the needle is removed with the wire guide remaining in a locked position distally about the lesion for guiding the surgeon to the lesion site during subsequent surgery.

20 Claims, 2 Drawing Sheets

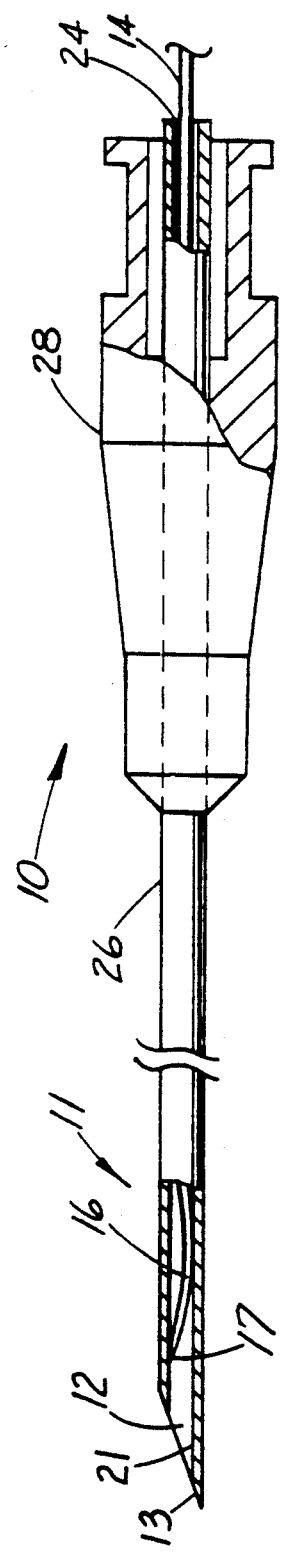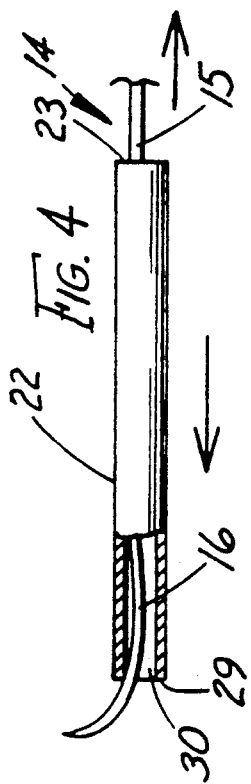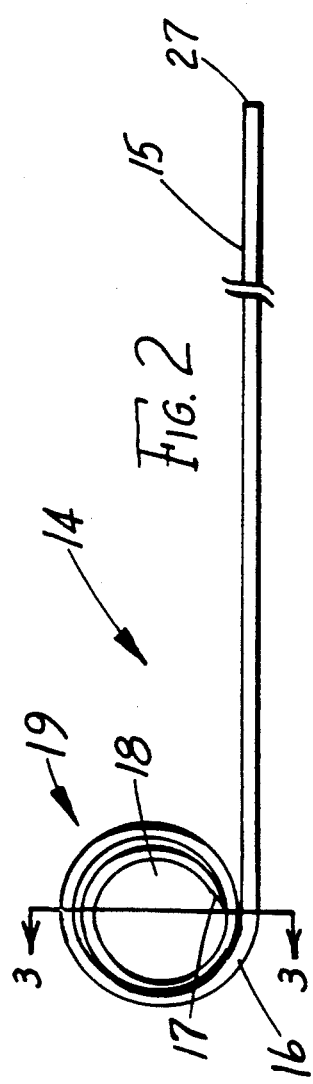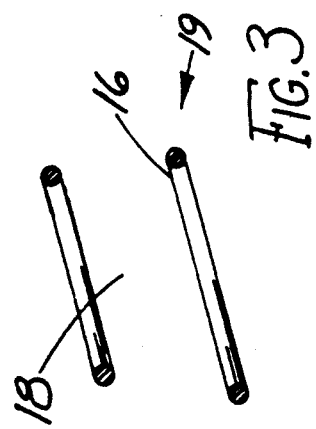

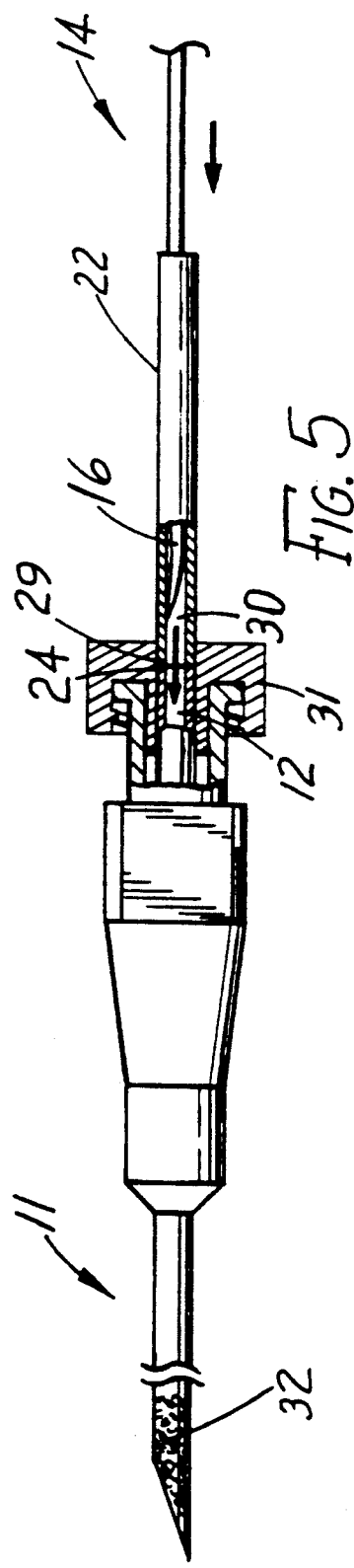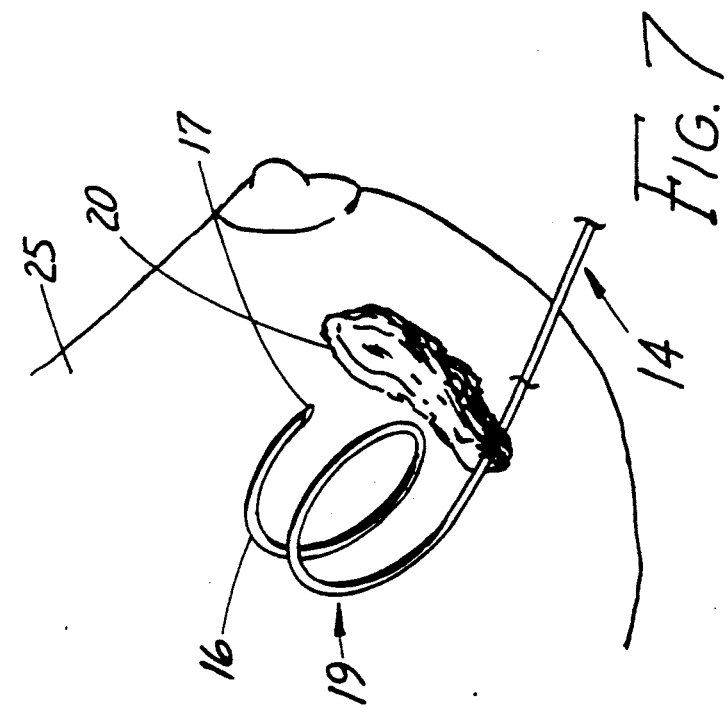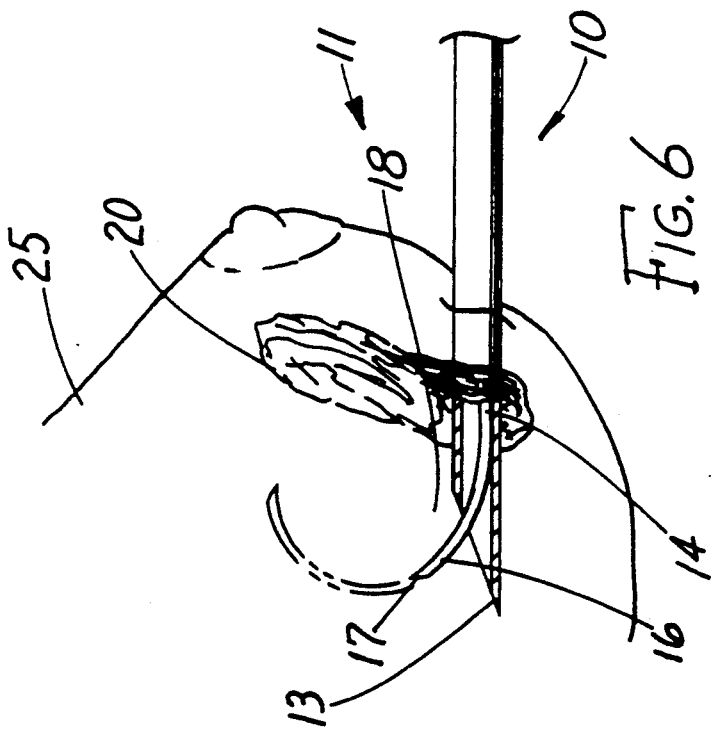

GUIDE FOR LOCALIZING A NONPALPABLE BREAST LESION

TECHNICAL FIELD

This invention relates to medical devices for localizing lesions within the body and, in particular, to a guide for the localization of a nonpalpable lesion within the breast.

BACKGROUND OF THE INVENTION

Localization needles or wire guides are utilized for preoperative marking of nonpalpable breast lesions. Typically, a needle cannula having a wire guide contained therein is inserted into the female breast and preferably positioned within two centimeters of the lesion. A mammogram or other visualization aid is used to confirm the position of the distal needle end. If the needle is not accurately positioned with respect to the lesion, the needle is repositioned, and another mammogram is taken to visualize the repositioning of the needle end with respect to the lesion. When the needle position is acceptable, the wire guide is extended from the distal end to localize the breast lesion for recision by the surgeon. Alternatively, the wire guide is maintained in a fixed position while the needle is removed to expose the wire guide contained therein. Similarly, the distal end of the wire guide localizes the breast lesion for recision by the surgeon. A number of prior art wire guides are utilized for localizing breast lesions. One in particular is the Kopans breast lesion localization needle that includes a spring-hook wire guide that is manufactured by Cook, Inc. of Bloomington, Ind. After the spring-hook wire guide is extended from the localization needle adjacent the breast lesion, the spring-hook wire guide remains relatively fixedly positioned. The guide may be further extended into the breast tissue either intentionally or unintentionally; however, the spring-hook prevents inadvertent removal of the wire guide from the breast tissue. This advantageously prevents retraction or removal of the wire guide due to inadvertent movement of the breast during transportation or movement of the patient. However, it does not prevent inadvertent advancement into the breast. Repositioning of the spring-hook wire guide is limited, and removal is by surgical resection.

A number of repositionable localization systems are also presently available. The HAWKINS TM breast lesion localization system manufactured by Boston Scientific Corporation of Watertown, Mass., includes a rigid cannula with a retractable side barb for repositioning the needle cannula if necessary. Some physicians prefer the rigid cannula; however, others do not. The rigid cannula also presents the risk of further penetration through the breast and into the chest cavity and lungs as a result of patient movement.

Another repositionable localization system is the Homer MAMMALOCK TM needle/wire localizer, which is available from Namic ® of Glens Falls, N.Y. The MAMMALOCK localizer includes a needle with a unique alloy J-hook wire positioned within the needle, which is extendable therefrom. The needle is introduced into the breast tissue, and the J-hook wire advanced into the tissue before a mammogram is taken for accuracy of placement. The J-hook wire tip protects the breast tissue from needle point penetration during breast compression. However, the J-hook tip includes a straight segment at the distal end which presents a significant disadvantage should the needle be removed. The curved portion of the J-hook wire tip does not track the straight segment at the distal end of the wire when extended from the distal end of the needle. As a result, the J-hook wire tip does not penetrate the tissue and is deflected from the lesion should the needle be subsequently removed. The deflection and lack of tractability significantly increase the difficulty of accurate placement of the wire guide. Trial-and-error placement of the guide also subjects the patient to unnecessary radiation received during the taking of extra mammograms.

Another repositionable wire guide having a memory hook for localizing breast lesions is disclosed in U.S. Pat. No. 4,616,656. This wire guide includes a relatively small hook with a pointed distal end. The wire guide is preferably made of a memory characteristic material which assumes the J-hook configuration in response to body heat. The J-hook may be repositioned after retraction into a sheath and re-extension into a new position. When the wire guide is acceptably positioned, the cannula is removed, and the wire guide is left as a guide for surgical excision of the lesion. This repositionable wire guide is also subject to the same disadvantages as those of the MAMMALOCK J-hook wire guide. Furthermore, the J-hook wire guide does not fixedly position or lock in breast tissue and is easily dislodged during transportation or movement of the patient. In addition, the J-hook wire tip design is hard for the surgeon to palpate.

SUMMARY OF THE INVENTION

The foregoing problems are solved and a technical advantage is achieved with an illustrative wire guide for localizing a nonpalpable lesion in a breast. The wire guide includes a distal portion including a superelastic metallic alloy and is preformed into a resilient helical coil configuration. This resilient helical coil configuration advantageously locks the wire guide into position once extended from the end of the introducing needle. The helical coil configuration of the wire guide includes an acuate or pointed distal end for penetrating the tissue as it extends from a tubular introducer needle. The resilient helical coil configuration includes at least more than a 180 degree turn which follows a path scribed by the acuate distal end as the distal portion is extended from the passageway of the introducer needle. This helical coil configuration may be easily palpated by the physician and includes a passageway that extends longitudinally through the configuration and laterally from the straight portion of the wire guide from which the distal portion extends. This lateral orientation further locks the guide in position should an extraction force be applied to the proximal end of the guide. The lateral orientation also advantageously prevents the wire guide, as well as the introducer needle, from being inadvertently extended further into the breast or chest cavity. As a result, this helical coil configuration with a lateral orientation provides a significant advantage over prior art J-hook tip designs as well as that of a corkscrew having a passageway with a longitudinal orientation.

The distal portion of the wire guide includes a superelastic metallic alloy having a transformation temperature below that of the normal operating environment of the guide. This superelastic metallic alloy includes nickel and titanium and resists deformation as a stress is applied. Furthermore, the superelastic metallic alloy wire returns to its preformed helical coil configuration when the deformation force is removed. This advantageously allows the helical coil configuration of the distal portion of the wire guide to be retracted within the introducer needle for repositioning.

The wire guide is combined with a tubular introducer needle for insertion into the breast to the site of the lesion. The distal end of the needle includes a plurality of indentations for advantageously enhancing the ultrasound visualization thereof. The distal portion of the wire guide assumes an unwound configuration when positioned within the passageway of the introducer needle. As the wire guide is extended from the tapered distal end of the needle, the distal portion assumes the resilient helical coil configuration about the lesion. The interior surface of the needle cannula is, for example, plug-drawn to provide a smooth surface about the passageway of the needle. This smooth surface prevents the pointed distal end of the guide from catching and lodging within the passageway of the introducer needle.

The medical device also includes a second cannula for back loading the wire guide into an introducer needle that has already been positioned within the breast. The second cannula also includes a smooth interior surface for repositioning the distal portion of the wire guide from the passageway of the second cannula into the passageway of the tubular introducer needle. A connector cap is also advantageously included and has a passageway extending longitudinally therein and sized for receiving the abutting cannula ends and aligning the passageways thereof.

The resilient helical coil configuration includes at least one turn of more than 180 degrees for fixedly positioning and locking the distal portion of the wire guide about the breast lesion. The helical coil configuration follows a path scribed by the acuate distal end to lock the distal portion of the guide advantageously without deflecting the guide or the introducer needle. The lateral orientation of the helical coil configuration also advantageously further locks the guide into position when the straight portion of the guide is pulled at the proximal end thereof.

BRIEF DESCRIPTION OF THE DRAWING

FIG. 1 depicts an illustrative preferred embodiment of a medical device of the present invention including a tubular introducer needle and a wire guide positioned therein for localizing a nonpalpable breast lesion;

FIG. 2 depicts the wire guide of FIG. 1 with its distal portion assuming a preformed resilient helical coil configuration;

FIG. 3 depicts a cross-sectional view of the distal portion of the wire guide of FIG. 2;

FIG. 4 depicts the wire guide of FIG. 1 positioned within a back loading cannula;

FIG. 5 depicts the transfer of the wire guide from the back loading cannula of FIG. 4 into the tubular introducer needle of FIG. 1; and FIGS. 6 and 7 depict the insertion of the medical device of FIG. 1 into a breast for localizing a nonpalpable breast lesion.

DETAILED DESCRIPTION

Depicted in FIG. 1 is an illustrative embodiment of medical device 10 comprising a tubular introducer needle 11 and a wire guide 14 positioned in passageway 12 of the needle for insertion into a breast to the site of a nonpalpable lesion. With a visualization aid such as an X-ray film or ultrasound, a radiologist typically inserts the needle with the wire guide positioned therein into the breast to the site of the lesion. When inserted, the radiologist extends distal portion 16 of the wire guide from tapered distal end 13 of the needle, which assumes a preformed resilient conical helical coil configuration distally about the breast lesion. Another X-ray or ultrasound is taken to confirm the positioning of the needle and the wire guide distally about the breast lesion. Should the needle and wire guide not be appropriately positioned, the distal portion of the wire guide is retracted into the passageway of the needle. The needle and wire guide are then repositioned within the breast closer to the lesion, and another X-ray or ultrasound is taken to confirm the repositioning of the needle and extended distal portion of the wire guide. After the needle and wire guide are properly positioned, the needle is removed from the breast with the wire guide and the distal portion thereof in the helical coil configuration, thereby locking the guide in a position distal to the lesion to guide the surgeon to resect the lesion within a wedge of breast tissue surrounding the wire guide.

Needle 11 comprises cannula 26 having passageway 12 extending longitudinally therethrough between proximal end 24 and tapered distal end 13 for positioning the wire guide therein. Cannula 26 is a 20-gauge thin-wall, plug-drawn stainless steel tube, which is commercially available from K-Tube Corporation, San Diego, Calif. The plug-drawn stainless steel tube provides cannula 26 with a smooth, seamless interior surface 21 which prevents the pointed distal end 17 of the wire guide from catching and lodging on the interior surface of the needle. Needle 11 is approximately 11.5 cm in length and is silicone coated for easy insertion into the breast. Cannula 26 includes distal end 13 tapered in a well-known venous bevel and proximal end 24 with a well-known female Luer-lock connector hub 28 insert molded thereabout for ease of handling and for connection to a syringe for injection and irrigation of fluids.

Depicted in FIG. 2 is wire guide 14 with straight portion 15 and distal portion 16 preformed into a resilient conical helical coil configuration 19. The wire guide and, in particular, distal portion 16 is comprised of a superelastic metallic alloy such as nitinol which is commercially available from, for example, Nitinol, Saratoga, Calif. or U.S. Shape Memory Applications, Inc., Sunnyvale, Calif. This superelastic metallic alloy in the preferred embodiment is nickel and titanium based and has a predetermined transformation temperature below that of the normal operating environment of the wire guide. In particular, the transformation temperature of wire guide 14 is in the range of 0–10 degrees Celsius, which is well below the body temperature of patients into whom the wire guide is to be inserted. When positioned in the passageway of a cannula such as that of needle 11, preformed distal portion 16 assumes an unwound configuration as depicted in FIG. 1.

By way of example, wire guide 14 comprises approximately 20.5 cm of 0.013 inch diameter nitinol wire sized for insertion through passageway 12 of tubular introducer needle 11. As depicted in FIG. 2, wire guide 14 includes proximal portion 27 and distal portion 16, which is preformed into a resilient conical helical coil configuration 19 having acuate distal end 17 for cutting into and locking distally about the nonpalpable breast lesion. As shown, the helical coil configuration of distal end 16 includes approximately two complete turns. This helical coil configuration preferably includes at least more than one 180 degree turn to assume a minimum locking position. A cylindrical helical coil configuration is also contemplated. The resilient helical coil configuration 19 follows a path scribed by acuate distal tip 17 as distal portion 16 is extended from passageway 12 of the needle to localize the nonpalpable breast lesion. Passageway 18 extending longitudinally through the helical coil configuration is laterally oriented with respect to straight portion 15. The lateral orientation locks the distal portion in place and prevents removal from or further insertion about the breast lesion when the straight portion is either pulled or pushed.

Depicted in FIG. 3 is a cross-sectional view of distal portion 16 having acuate distal end 17 taken along the line 3—3 of FIG. 2. This cross-sectional view of the distal portion illustrates the conical helical coil configuration 19 of the wire guide with longitudinal passageway 18 extending therethrough.

Depicted in FIG. 4 is back loading cannula 22 for positioning wire guide 14 therein and loading the wire guide into needle 11 after the needle has been positioned into, for example, the breast. Back loading cannula 22 is another piece of 20-gauge, thin-wall stainless steel tube similar to that of needle 11. As shown, straight portion 15 of the wire guide is inserted into the passageway 30 of the cannula through distal end 29 and out proximal end 23. The back loading cannula is brought into position with the conical helical coil configuration of distal portion 16 of the wire guide. The straight portion of the wire guide is pulled to retract the distal portion of the wire guide into the passageway of the back loading cannula. When fully retracted, the distal portion of the wire guide assumes an unwound configuration for positioning within the passageway of the needle.

To position the wire guide within the passageway of a positioned needle, distal end 29 of the back loading cannula is abutted against the proximal end 24 of the needle with male Luer-lock connector cap 31 as shown in FIG. 5. The cap includes a passageway therein for aligning the two passageways of the cannulas. When the two pieces of cannula are abutted together, the distal portion of wire guide 14 is extended from distal end 29 of passageway 30 and repositioned into passageway 12 of the needle while maintaining an unwound configuration. The distal end of the needle cannula is sandblasted or, preferably, includes a plurality of semispherical indentations 32 formed in the outer surface thereof to enhance the ultrasound imaging of the distal needle end. Such ultrasound-enhanced needles are commercially available from Cook Urological Incorporated, Spencer, Ind.

Depicted in FIGS. 6 and 7 is medical device 10 comprising tubular introducer needle 11 containing wire guide 14 which is inserted into a breast 25 for localizing nonpalpable breast lesion 20. Wire guide 14 is extended from distal end 13 of needle 11. As the wire guide emerges from the needle, acuate distal end 17 cuts into and scribes a conical helical path distally about the tissue surrounding the breast lesion. The remainder of distal portion 16 follows the helical path scribed by acuate distal end 17. In this manner, distal portion 16 resumes a preformed helical coil configuration 19 which includes longitudinal passageway 18 therethrough for holding and locking the distal portion of the wire guide distally about lesion 20. The resilient helical coil configuration resists being dislodged from its distal position about the lesion during subsequent movement of the patient.

It is to be understood that the above-described medical device including a wire guide having a preformed helical coil configuration is merely an illustrative embodiment of the principles of this invention and that other wire guides and configurations thereof for locking the guide distally about a breast lesion may be devised by those skilled in the art without departing from the spirit and scope of this invention. In particular, the distal portion of the wire guide may be preformed into any resilient configuration which is assumed when extended from the distal end of an introducer needle. It is contemplated that other superelastic alloys may be utilized with the distal portion of the guide for assuming the preformed locking configuration as well as being able to retract into the introducer needle for repositioning about the lesion. A conical or cylindrical helical coil configuration having a passageway extending longitudinally from the straight portion of the guide is also contemplated.

What is claimed is:

1. A wire guide for localizing a nonpalpable lesion in a breast comprising:
   a straight portion; and
   a distal portion preformed into a resilient configuration of substantially more than a 180 degree turn, said distal portion including a superelastic material such that said resilient configuration of said distal portion can be repeatably and smoothly inserted into and smoothly withdrawn from the region of the lesion characterized in that said resilient configuration of said distal portion assumes an unwound configuration when positioned in a passageway of a tubular introducer needle, said distal position assuming a resilient helical coil configuration as said distal portion of said wire guide is extended from a passageway of a needle, said resilient helical coil configuration including a longitudinal passageway extending laterally from said straight portion.

2. A wire guide for localizing a nonpalpable lesion in a breast comprising:
   a straight portion; and
   a distal portion including a superelastic metallic alloy and having an unwound configuration when positioned in a passageway of a cannula and a preformed, resilient helical coil configuration extending laterally from said straight portion when positioned out of a passageway of a cannula.

3. The wire guide of claim 2 wherein said resilient helical coil configuration includes at least more than a 180 degree turn.

4. The wire guide of claim 2 wherein said resilient helical coil configuration of said distal portion includes an acuate distal end.

5. The wire guide of claim 2 further comprising a cannula including a passageway extending longitudinally therethrough.

6. The wire guide of claim 2 wherein said superelastic metallic alloy includes nickel and titanium.

7. The wire guide of claim 2 wherein said superelastic metallic alloy has a predetermined transformation temperature and wherein said superelastic metallic alloy is normally operated above said predetermined transformation temperature.

8. A medical device for localizing a nonpalpable lesion in a breast comprising:

a tubular needle having a passageway extending longitudinally therethrough and a distal end tapered for insertion into said breast to the site of said lesion; and a wire guide for insertion into said passageway of said needle and having a straight portion and a distal portion, said distal portion including a superelastic metallic alloy, a preformed, resilient helical coil configuration extending laterally from said straight portion when positioned out of said passageway of said tubular needle, and an unwound configuration when positioned in said passageway of said tubular needle.

9. The device of claim 8 wherein said resilient helical coil configuration includes at least more than a 180 degree turn.

10. The device of claim 8 wherein said distal portion includes an acuate distal end.

11. The device of claim 8 wherein said resilient helical coil configuration of said distal portion includes at least one turn and an acuate distal end, said at least one turn following a path scribed by said acuate distal end as said distal portion is extended from said passageway of said needle.

12. The device of claim 8 wherein said superelastic metallic alloy includes nickel and titanium.

13. The device of claim 8 wherein said superelastic metallic alloy has a predetermined transformation temperature.

14. The device of claim 8 wherein said needle comprises a first cannula including said passageway and a predetermined interior surface about said passageway.

15. The device of claim 14 wherein said predetermined interior surface is a plug-drawn surface.

16. The device of claim 8 wherein said tubular needle has a plurality of indentations in an outer surface thereof about said tapered distal end.

17. The device of claim 16 wherein said indentations are at least partially semispherical.

18. A medical device for localizing a nonpalpable lesion in a breast comprising:
a tubular needle comprising a first cannula having a passageway extending longitudinally therethrough, a predetermined interior surface about said passageway, and a distal end tapered for insertion into said breast to the site of said lesion;

a wire guide for insertion into said passageway of said tubular needle and having a straight portion and a distal portion, said distal portion including a superelastic metallic alloy, a preformed, resilient helical coil configuration when positioned out of said passageway of said tubular needle, and an unwound configuration when positioned in said passageway of said tubular needle; and a second cannula having a distal end and a passageway extending longitudinally therethrough, said distal portion of said wire guide for insertion into said passageways of said first and second cannulas assuming said unwound configuration when positioned in said passageway of said second cannula, said first cannula including a proximal end, said distal end of said second cannula abutting against said proximal end of said first cannula when transferring said distal portion of said wire guide in said unwound configuration from said passageway of said second cannula to said passageway of said first cannula.

19. The device of claim 18 further comprising a cap having a passageway extending longitudinally therein sized for receiving said first and second cannulas and aligning said passageways thereof.

20. A medical device for localizing a nonpalpable lesion in a breast comprising:
a tubular introducer needle including a first cannula having a first distal end tapered for insertion into said breast to the site of said lesion, a first proximal end, a first passageway extending longitudinally between said first ends, a plug-drawn interior surface about said first passageways, and an outer surface having a plurality of semispherical indentations therein about said first distal end;

a second cannula including a second distal end, a second proximal end, a second passageway extending longitudinally between said second ends and a second plug-drawn interior surface about said second passageway;

a connector having a passageway extending longitudinally therein and sized for receiving said first and second cannulas and aligning said passageways thereof; and a wire guide for insertion in said first and second passageways of said first and second cannulas and having a straight portion and a distal portion, said distal portion including a superelastic, nickel and titanium metallic alloy and a preformed, resilient helical coil configuration including at least more than a 180 degree turn, an acuate distal end, and a passageway extending longitudinally through said preformed, resilient helical coil configuration and laterally from said straight portion, said alloy having a predetermined transformation temperature, said distal end portion assuming an unwound configuration when positioned in said first passageway of at least one of said first and second cannulas, said at least more than a 180 degree turn following a path scribed by said acuate distal end as said distal portion is extended from said first passageway at said tapered first distal end of said first cannula, said second distal end of said second cannula abutting against said first proximal end of said first cannula when transferring said distal portion of said wire guide in said unwound configuration from said second passageway of said second cannula to said first passageway of said first cannula.

* * * * *